United States Patent
Lishchiner et al.

(10) Patent No.: US 10,131,592 B2
(45) Date of Patent: Nov. 20, 2018

(54) CATALYST AND METHOD FOR AROMATIZATION OF $C_3$—$C_4$ GASES, LIGHT HYDROCARBON FRACTIONS AND ALIPHATIC ALCOHOLS, AS WELL AS MIXTURES THEREOF

(71) Applicant: NGT GLOBAL AG

(72) Inventors: Iosif Izrailevich Lishchiner, Moscow (RU); Olga Vasilyevna Malova, Moscow (RU); Andrey Leonidovich Tarasov, Moscow (RU)

(73) Assignee: NGT Global AG, Zug (CH)

( * ) Notice: Subject to any disclaimer, the term of this patent is extended or adjusted under 35 U.S.C. 154(b) by 0 days.

(21) Appl. No.: 15/113,147

(22) PCT Filed: Dec. 17, 2014

(86) PCT No.: PCT/RU2014/000953
§ 371 (c)(1),
(2) Date: Jul. 21, 2016

(87) PCT Pub. No.: WO2015/115932
PCT Pub. Date: Aug. 6, 2015

(65) Prior Publication Data
US 2017/0007992 A1    Jan. 12, 2017

(30) Foreign Application Priority Data
Jan. 28, 2014   (RU) ................ 2014102625

(51) Int. Cl.
| | |
|---|---|
| *C07C 2/86* | (2006.01) |
| *B01J 29/40* | (2006.01) |
| *B01J 29/80* | (2006.01) |
| *C10G 35/06* | (2006.01) |
| *B01J 29/06* | (2006.01) |
| *B01J 21/04* | (2006.01) |

(Continued)

(52) U.S. Cl.
CPC ............ *C07C 2/864* (2013.01); *B01J 21/04* (2013.01); *B01J 21/08* (2013.01); *B01J 29/061* (2013.01); *B01J 29/40* (2013.01); *B01J 29/405* (2013.01); *B01J 29/80* (2013.01); *B01J 35/0006* (2013.01); *B01J 37/04* (2013.01); *B01J 37/30* (2013.01); *C10G 35/065* (2013.01); *B01J 2029/062* (2013.01); *B01J 2229/183* (2013.01); *B01J 2229/38* (2013.01); *C07C 2521/04* (2013.01); *C07C 2521/08* (2013.01);CPC .......... *C07C 2529/40* (2013.01); *C07C 2529/80* (2013.01); *C10G 2300/104* (2013.01); *C10G 2300/1044* (2013.01); *C10G 2400/30* (2013.01)

(58) Field of Classification Search
CPC ............ B01J 29/40; B01J 29/45; B01J 29/80
See application file for complete search history.

(56) References Cited

U.S. PATENT DOCUMENTS

| | | | | |
|---|---|---|---|---|
| 4,424,401 A | * | 1/1984 | White ................. | C07C 2/00 585/14 |
| 6,277,355 B1 | * | 8/2001 | Kennedy ............... | C01B 39/365 423/705 |
| 2004/0029716 A1 | * | 2/2004 | Mohr ................. | B01J 29/06 502/67 |
| 2017/0145317 A1 | * | 5/2017 | Lischiner ............. | C10G 35/095 |

FOREIGN PATENT DOCUMENTS

RU        2429910 C1 *  9/2011

OTHER PUBLICATIONS

RU 2429910 machine translation. Sep. 27, 2011.*
International Search report PCT/RU2014/000953 with translation of ISR, 2015.
PCT/RU2014/000953 Opinion, 2015.

*Primary Examiner* — Philip Y Louie
*Assistant Examiner* — Alyssa L Cepluch
(74) *Attorney, Agent, or Firm* — Glen P. Belvis; Belvis Law, LLC.

(57) ABSTRACT

The invention relates to hydrocarbon feedstock processing technology, in particular, to catalysts and technology for aromatization of $C_3$-$C_4$ hydrocarbon gases, light low-octane hydrocarbon fractions and oxygen-containing compounds ($C_1$-$C_3$ aliphatic alcohols), as well as mixtures thereof resulting in producing an aromatic hydrocarbon concentrate (AHCC). The catalyst comprises a mechanical mixture of 2 zeolites, one of which is characterized by the silica/alumina ratio $SiO_2/Al_2O_3=20$, pre-treated with an aqueous alkali solution and modified with oxides of rare-earth elements used in the amount from 0.5 to 2.0 wt % based on the weight of the first zeolite. The second zeolite is characterized by the silica/alumina ratio $SiO_2/Al_2O_3=82$, comprises sodium oxide residual amounts of 0.04 wt % based on the weight of the second zeolite, and is modified with magnesium oxide in the amount from 0.5 to 5.0 wt % based on the weight of the second zeolite. Furthermore, the zeolites are used in the weight ratio from 1.7:1 to 2.8:1, wherein a binder comprises at least silicon oxide and is used in the amount from 20 to 25 wt % based on the weight of the catalyst. The process is carried out using the proposed catalyst in an isothermal reactor without recirculation of gases from a separation stage, by contacting a fixed catalyst bed with a gaseous feedstock, which was evaporated and heated in a preheater. The technical result consists in achieving a higher aromatic hydrocarbon yield while ensuring almost complete conversion of the HC feedstock and oxygenates, an increased selectivity with respect to forming xylols as part of an AHCC, while simultaneously simplifying the technological setup of the process by virtue of using a reduced (inter alia, atmospheric) pressure.

7 Claims, No Drawings

(51) Int. Cl.
*B01J 21/08* (2006.01)
*B01J 35/00* (2006.01)
*B01J 37/04* (2006.01)
*B01J 37/30* (2006.01)

* cited by examiner

CATALYST AND METHOD FOR AROMATIZATION OF $C_3$—$C_4$ GASES, LIGHT HYDROCARBON FRACTIONS AND ALIPHATIC ALCOHOLS, AS WELL AS MIXTURES THEREOF

The present application is the National Stage (§ 371) of International Application No. PCT/RU2014/000953, filed Dec. 17, 2014, which claims priority from Russian Patent Application No. 2014102625, filed Jan. 28, 2014, both incorporated herein by reference.

The invention relates to technology for processing hydrocarbon feedstock, in particular, to catalysts and technology for aromatization of $C_3$-$C_4$ hydrocarbon gases, light low-octane hydrocarbon fractions (in particular, of a wide fraction of light hydrocarbons (WFLH), gas condensates and straight-run gasolines, and also of light naphtha of the Fischer-Tropsch et al. process) and oxygen-containing compounds ($C_1$-$C_3$ aliphatic alcohols), as well as mixtures thereof, so as to produce an aromatic hydrocarbon concentrate (AHCC).

The invention can be used in the oil-refining and hydrocarbon processing industry for blending straight-run gasolines using an obtained high-octane AHCC, and also for obtaining individual aromatic hydrocarbons (benzene, toluene, xylenes), which are isolated during fractionation of the AHCC and are widely popular solvents and reagents for obtaining more complex organic substances, for example, cumene.

In traditional methods for aromatization, the feedstock is the carrier of the heat energy necessary for carrying out an aromatic hydrocarbon formation reaction. In order to achieve a high degree of conversion of the feedstock, it is necessary to significantly overheat said feedstock in relation to the reaction temperature, which leads to rapid coking of the catalyst and tubes of the heat exchangers. In the present invention, the problem of the energy supply for an endothermic reaction of aromatization of paraffinic hydrocarbons (H/C) is solved by directly introducing into the reaction zone oxygenates ($C_1$-$C_3$ aliphatic alcohols), which, upon dehydration, release the heat energy necessary to provide for a high degree of conversion of the H/C feedstock into aromatic hydrocarbons (ArH).

Attempts to implement a process of aromatization of light paraffin hydrocarbons were undertaken in the beginning of the 1990s. The most well-known and developed is the "Cyclar" process, a joint development of British Petroleum and Universal Oil Products. The process uses an installation with a fluidized catalyst bed, a development of the Universal Oil Products Company, with regeneration of the coked catalyst outside of the reactor and recirculation of unconverted products. For hydrogen separation in this process, the use of a cryogenic section is proposed. Liquefied petroleum gases, which are mainly propane and butane, are used as the feedstock. The aromatic hydrocarbon yield based on the converted feedstock is 55-63% by weight, depending on the composition of the feedstock. This process was brought to an experimental-industrial level and was then placed on hold due to the economic inexpediency of the industrial implementation thereof.

RF patent no. 2377230 describes a method for aromatization of light alkanes containing between one and four carbon atoms, which involves contacting a gas feedstock with a Pt/ZSM-5 catalyst containing platinum deposited on an MFI zeolite, the lattice of which consists of aluminum, silicon and oxygen. The use of this catalyst in the process of aromatization of alkanes suppresses methane formation and increases selectivity based on a benzene-toluene-xylene fraction. The high ethane content relative to the amount of methane in the light gas fraction makes it possible to use off-gas as feedstock for a cracker.

The process of aromatization of light paraffin $C_5$-$C_7$ hydrocarbons is also, as in the case of a propane-butane fraction, based on the following reactions: cracking, oligomerization, disproportionation, dehydrocyclization, and dealkylation. As a result of the cracking reaction, $C_2$-$C_4$ olefins are formed, which enter into the oligomerization reaction so as to form olefin $C_6$-$C_{12}$ hydrocarbons, which thereafter in the course of the dehydrocyclization reaction form aromatic hydrocarbons.

In RF patent no. 2163623, low-octane straight-run gasoline fractions are subjected to reforming in the presence of monobasic or dibasic alcohols, taken in a quantity of 0.2-5.0 wt. %. The catalyst of the process is a mechanical mixture of two catalysts: a zeolite-containing catalyst and an aluminum-cobalt (nickel)-molybdenum oxide catalyst. The process is carried out at a temperature of 460-510° C. and at a liquid space velocity of feedstock supply of 0.3-0.9 $h^{-1}$. An advantage of said method is the possibility of substantially (by 10-15 points) increasing the gasoline octane numbers; however, a disadvantage of said method is the high temperature of the process, low capacity due to the low liquid space velocity of feedstock supply, and high sensitivity of the oxide catalyst to sulfur-containing impurities.

RF patent no. 2337127 describes a method for catalytic reforming of gasoline fractions in the presence of a hydrogen-containing gas in a system formed of multiple successively connected reactors with platinum-containing catalysts under elevated pressure and temperature, which is carried out in three stages. At the first stage, aromatization of cycloalkanes and alkanes is carried out by contacting hydrocarbon components with an aluminum-platinum-rhenium catalyst at a mass velocity of feedstock supply based on the catalyst mass of 4-8 $h^{-1}$ and at a temperature of 460-480° C.; at the second stage, hydroisomerization of arenes, cycloalkanes and alkanes is carried out on a zircon-sulfate catalyst containing platinum, at a mass velocity of feedstock supply based on the catalyst mass of no less than 8 $hours^{-1}$ and at a temperature of 150-200° C.; and at the third stage, aromatization of the cycloalkanes is again carried out on an aluminum-platinum-rhenium catalyst at a mass velocity of feedstock supply based on the catalyst mass of no less than 8 $hours^{-1}$ and at a temperature of 360-400° C.; furthermore, the pressure at the inlet of the system of reforming reactors is 1.5 MPa, and the hydrogen-containing gas enters the inlet of the reactor system in an amount corresponding to the molar ratio of hydrogen/feedstock of at least 8. The disadvantages of said method are the use of expensive catalysts containing precious metals, and also the complexity of the process flow scheme, since the use of multiple successively connected reactors operating under an elevated pressure is proposed.

RF patent no. 2307117 describes a method for producing a catalyst for aromatization and a method for aromatization of alkanes having between two and six carbon atoms in a molecule. A method for aromatization of hydrocarbons is described, which involves: (a) contacting an alkane, containing between 2 and 6 carbon atoms in a molecule, with at least one catalyst containing an aluminum-silicon-germanium zeolite, on which platinum is deposited; and (b) separating the aromatization product. A method for synthesizing an aluminum-silicon-germanium-platinum zeolite catalyst is described, which involves the following stages: (1): a zeolite is obtained, which contains aluminum, silicon and germanium; (2) platinum is deposited on a microporous aluminum-silicon-germanium zeolite; and (3) the zeolite is calcined. A method for pre-treating a catalyst for aromatization of hydrocarbons is also described, which involves the following stages: (1) platinum is deposited on an aluminum-silicon-germanium zeolite; (2) the catalyst is additionally treated using hydrogen and then using a sulfur compound; and (3) the catalyst is treated with hydrogen a second time. The technical effect is increased stability of the catalyst. However, a considerable disadvantage of this and other traditional methods of aromatization (reforming) is the low ArH yield and the use of precious metals in the composition of the catalyst.

RF patent no. 2372988 describes a catalyst for converting $C_2$-$C_{12}$ aliphatic hydrocarbons and/or $C_1$-$C_{12}$ aliphatic oxygen-containing compounds into high-octane gasoline or aromatic hydrocarbons, said catalyst comprising a pentasil zeolite, an aromatization promoter i.e. zinc, and a binding agent. Said zeolite is characterized by a value of the $SiO_2$/$Al_2O_3$ molar ratio in the range of 20-80 with a residual sodium ion content of less than 0.1%; the aromatization promoter is introduced using any of the known methods, with the following ratio of components: zeolite—30.0-90.0 wt. %; zinc—0.5-8.0 wt. %; binding agent—the remainder; furthermore, the catalyst is additionally treated using an ammonium fluoride solution after the introduction of zinc thereto.

The technical effect is the creation of a highly-active and stable catalyst, providing for processing of a wide range of hydrocarbon-containing feedstock. A disadvantage of said catalyst is the rapid decline in the activity thereof and, as a result, the need for frequent oxidative regenerations of the catalyst.

The prior art of the developed method is RF patent no. 2440189, which describes a similar catalyst for producing high-octane gasolines with a low content of benzene and durene, in which an augmentation of the octane ratings of the finished gasoline is achieved in the course of the aromatization of the paraffin H/C in the initial feedstock, so as to produce a high-octane fraction of aromatic H/C (FAH). A mechanical mixture is used as the catalyst, which comprises a pentasil zeolite with a $SiO_2$/$Al_2O_3$ molar ratio=18-25, which does not contain modifiers and is pre-treated using an aqueous alkali solution, and a pentasil zeolite with a $SiO_2$/$Al_2O_3$ molar ratio=70-90, which is modified by magnesium oxide in a quantity of 0.5-3.0 wt. %, taken in a ratio of between 1/1 and 1/10, and also a binding agent in a quantity of between 20 and 25 wt. % of the mass of the catalyst. A method is also described for producing high-octane gasolines with a high (up to 50 wt. %) aromatics content. The catalyst is heated in an isothermal reactor with heat pipes to a temperature of 280-320° C., while the process of contacting the feedstock with the catalyst heated in the isothermal reactor with heat pipes is carried out under a pressure of 0.1-1 MPa when supplying feedstock to the reactor with a space velocity of 1-5 $h^{-1}$ (in terms of liquid) and when supplying an inert gas at a gaseous space velocity of 1000-10,000 h after evaporation of the feedstock in the pre-heater. A considerable disadvantage of the proposed method is the fact that in order to subsequently produce individual ArH (benzene, toluene, xylenes) from gasoline with an ArH content no higher than 50.2%, rather complex extraction fractionation is required, since there are aliphatic H/C present in the composition of the FAH.

The prior art closest to the developed invention is RF patent no. 2277524, which characterizes a method for producing aromatic hydrocarbons from hydrocarbon feedstock containing aliphatic hydrocarbons. When carrying out the method, a catalyst is used which is manufactured according to RF patent no. 2165293, and which has the following composition in wt. %: a pentasil zeolite ($SiO_2$/$Al_2O_3$=60, sodium oxide content of less than 0.1 wt. %)—62; zinc oxide—1.8; cerium oxide—0.3; lanthanum oxide—1.5; magnesium oxide—0.2; aluminum oxide—34.2. The method for aromatization includes the conversion of feedstock (a propane-butane fraction, containing 0.8 wt. % ethane, 14.0 wt. % propane, 1.5 wt. % isobutane and 80.6 wt. % n-butane and 3.1 wt. % pentane) when contacting same with a catalyst separated into two zones which differ in the conditions of conversion of aliphatic hydrocarbons into aromatic hydrocarbons, and in order to separate $C_{5+}$ hydrocarbons (AHCC), which contain aromatic hydrocarbons, from the obtained products, the feedstock is directed into a low-temperature zone for conversion of the more active aliphatic hydrocarbons; a stream of $C_{5+}$ hydrocarbons is separated from the obtained product, and the remaining hydrocarbons of the product of the low-temperature zone are directed into a high-temperature zone for conversion of the less active aliphatic hydrocarbons. The AHCC yield in one pass of the feedstock does not exceed 38.4%, wherein the xylene content in the AHCC is 21.8%. Conversely, when using recirculation of separation gases (in stream 13) with a yield of 52.6% on the feedstock, AHCC is produced with a total aromatics content of 94.1% (benzene 14.1%, toluene 45.3%, xylenes 23.0%, L10.7%).

The disadvantage of the proposed method is the very high temperature to which feedstock is heated in heat exchangers and furnaces (up to 575° C.), which leads to coking of heat exchangers, and also the high temperature of the process itself (520-550° C.). The complex implementation of the process should also be noted, since in two reaction zones (reactors) an elevated pressure is used (0.8-2.0 MPa), as well as recirculation of separation gases. Furthermore, without the use of recirculation of gases, for feedstock containing 85 wt. % $C_{4+}$ hydrocarbons a low ArH yield is observed.

The technical problem solved by means of the present invention involves the creation of a highly effective catalyst for aromatization of H/C feedstock and aliphatic alcohols, which provides for an increased yield of ArH in the resulting AHCC, as well as the development of a simpler and less energy-intensive method for aromatization of $C_3$-$C_4$ gases and light low-octane hydrocarbon fractions in mixtures with $C_1$-$C_3$ aliphatic alcohols, which differs in the increased content of highly sought after xylenes.

The technical result obtained when implementing the proposed invention involves the achievement of a higher yield of ArH, with almost complete conversion of H/C feedstock and oxygenates, increased selectivity with regard to the formation of xylenes in the composition of the AHCC, and with a simultaneous simplification of the technological implementation of the process as a result of the use of reduced (including atmospheric) pressure.

Furthermore, by using an additional quantity of aliphatic alcohols in the composition of the H/C feedstock and also higher volumetric gas feedstock space velocities, high ArH productivity values are achieved.

In order to achieve said technical result, a catalyst is proposed which contains a mechanical mixture of 2 pentasil zeolites with a different $SiO_2$/$Al_2O_3$ molar ratios: (1) a zeolite with $SiO_2$/$Al_2O_3$ molar ratio=20, which is pre-treated using an aqueous alkali solution, and which is modified by oxides of rare earth elements (REE)—0.5-2.0 wt. % of the mass of the first zeolite; and (2) a zeolite with $SiO_2$/$Al_2O_3$ molar ratio=82, which is modified by magnesium oxide—

0.5-5.0 wt. % of the mass of the second zeolite, which are taken in a mass ratio of between 1.7/1 and 2.8/1; with the remainder being a binding agent (preferably, silicon oxide, potentially with the addition of aluminum oxide in a quantity of up to 25 wt. % of the mass of the binding agent), in a quantity of between 20 and 25 wt. % of the mass of the catalyst.

The pre-treatment using an alkali and the modification of zeolites using REE and magnesium oxides were carried out at room temperature while impregnating the zeolites (by incipient wetness) with aqueous solutions of an alkali (NaOH), REE or magnesium nitrates.

A distinguishing feature of the catalyst is that, in the proposed catalyst, the composition of a mechanical mixture of 2 pentasil zeolites is dominated by a low-modulus zeolite with $SiO_2/Al_2O_3=20$ having an increased acidity, which, at elevated temperatures in the process, enables a more complete aromatization of the H/C portion of the feedstock so as to form AHCC, and also that the combined silica-alumina catalyst simultaneously has activity in aromatization reactions and in alkylation reactions of benzene with $C_2$-$C_4$ olefins formed (in situ) in the process of converting oxygenates, which leads to the production of AHCC with an increased content of xylenes.

The preferred use of silicon oxide as a binding agent for the catalyst, said silicon oxide not having acidic properties, in comparison with the binding agent used in the prior art invention, namely aluminum oxide, distinguishes the catalyst significantly by its reduced activity in cracking reactions, and leads to a greater ArH selectivity. Furthermore, the catalyst has greater mechanical strength during operation in areas of high temperatures in the presence of reaction water.

To achieve said technical result, it is proposed to use the method for aromatization of $C_3$-$C_4$ gases, low-octane hydrocarbon fractions and aliphatic alcohols, as well as mixtures thereof, which is proposed in the invention, according to which the catalyst, having the composition stated above, is heated in an isothermal reactor (see the prior art closest to the claimed invention) to a temperature of 400-500° C., and the process for contacting the gaseous feedstock, which is evaporated in a pre-heater and heated to a temperature of 150-250° C., with a catalyst is carried out under both atmospheric and elevated pressures (up to 18 atm) at a space velocity of 300-1500 $h^{-1}$ (for gas).

The use of mixtures of aliphatic alcohols and hydrocarbon feedstock facilitates the execution of the aromatization process under milder conditions because the heat energy released during the on-going exothermic conversion reactions accompanying the aromatization process, said conversion being the conversion of dimethyl ether (DME) (intermediate product formed during the dehydration of alcohols) to olefins, the oligomerization of olefins and alkylation of the lowest aromatics by oxygenates and olefins formed from the oxygenates, goes to feed the endothermic reaction of the aromatization of hydrocarbons. Consequently, and also as a result of the presence of water in the reaction mixture, said water being formed during the dehydration of the alcohols, a significant reduction in the methane- and coke-formation takes place, which leads to an increase in the period of stable operation of the catalyst.

Furthermore, the conversion of the feedstock in one pass and the lack of recirculation of separation gases in the proposed method substantially reduces the cost associated with carrying out the process.

A distinguishing feature of the proposed aromatization method is also a broader spectrum of H/C feedstock which can be in the form of a mixture of paraffin and olefin $C_3$-$C_4$ gases, WFLH, various gasolines (boiling point of up to 200° C.) and oxygenates, as well as mixtures of H/C with oxygenates ($C_1$-$C_3$ aliphatic alcohols) with an oxygenate content of between 10 and 50 vol. %.

The proposed method can be used in areas where there are gas condensate fields, associated petroleum gas, as well as sources of low-octane gasolines and alcohol production waste. The AHCC produced by the proposed method can be used to obtain individual ArH (including the sought-after xylenes) with the further use of same in chemical synthesis processes.

The invention is illustrated by the following examples:

EXAMPLE 1

A catalyst containing a mechanical mixture of 2 zeolites—75 wt. % in the composition of the catalyst: (1) a zeolite with a $SiO_2/Al_2O_3$ molar ratio=20, pre-treated with an aqueous alkali solution ($Na_2O$ content—0.5 wt. % based on this zeolite) and modified with lanthanum oxide—2.0 wt. %, and (2) a zeolite with $SiO_2/Al_2O_3$ molar ratio=82 with a residual quantity of sodium oxide of 0.04 wt. %, modified by magnesium oxide—0.5 wt. %, which are taken in the ratio 2.8/1; with the remainder being a binding agent—25 wt. % silicon oxide.

EXAMPLE 2

A catalyst containing a mechanical mixture of 2 zeolites—80 wt. % in the composition of the catalyst: (1) a zeolite with a $SiO_2/Al_2O_3$ molar ratio=20, pre-treated with an aqueous alkali solution ($Na_2O$ content—0.5 wt. % based on this zeolite) and modified with cerium oxide—0.5 wt. %, and (2) a zeolite with $SiO_2/Al_2O_3$ molar ratio=82 with a residual quantity of sodium oxide of 0.04 wt. %, modified by magnesium oxide—5.0 wt. %, which are taken in the ratio 1.7/1; with the remainder being a binding agent—20 wt. % (a mixture of aluminum oxide and silicon oxide taken in the mass ratio 1/4).

EXAMPLES 3-9

The process was carried out in an isothermal flow reactor with electric heating at a pressure in the range of 1-18 atm while contacting 100 $cm^3$ of the catalyst, which is prepared according to examples 1 and 2 (the catalyst bed height being 25 cm) and heated to temperatures of 400-500° C., with the feedstock gas, said feedstock gas being pre-heated in a pre-heater to 150-250° C. and in the form of $C_3$-$C_4$ H/C gases, various low-octane hydrocarbon fractions (WFLH) or gasolines and oxygenates (methanol, ethanol, isopropanol), as well as mixtures of H/C with alcohols, at a gas feedstock space velocity of 300-1500 $h^{-1}$.

The AHCC obtained during the reaction was accumulated over a period of 24 hours, and then the composition thereof was chromatographically determined according to ASTM 6729. In examples 6 and 10 (the comparison), continuous experiments were carried out for 300 hours.

The hydrocarbon composition of the feedstock is listed in table 1.

EXAMPLE 10 (COMPARATIVE EXAMPLE)

The process was carried out according to example 3, with the exception of the fact that the process was carried out at a temperature of 520° C. and at a pressure of 8 atm (as in the prior art invention), and a propane-butane fraction without oxygenate additives (methanol) was used as the feedstock.

TABLE 1

| Composition, wt. % | Wide fraction of light hydrocarbons (WFLH) | Propane-butane fraction (PBF) | Mixture of propane-propylene fraction (PPF) + butane-butylene fraction (BBF) (50/50 vol.) |
|---|---|---|---|
| methane | 0.1 | — | |
| ethane | 3.4 | 0.3 | |
| propane | 26.2 | 38.6 | 3.4 |
| propylene | — | | 28.5 |
| isobutane | 12.2 | 20.7 | 29.6 |
| n-butane | 25.0 | 35.9 | 6.8 |
| butylenes | — | | 31.7 |
| isopentanes | 10.3 | | |
| cyclopentane | 0.8 | | |
| n-pentane | 10.5 | 4.1 | |
| n-hexane | 3.0 | 0.4 | |
| isohexanes | 3.8 | | |
| cyclohexanes | 0.9 | | |
| heptanes | 2.9 | | |
| octanes | 0.9 | | |
| TOTAL | 100 | 100 | 100 |

Table 2 contains specific data regarding the conversion of different types of gas and liquid low-octane hydrocarbon feedstock and aliphatic alcohols, as well as mixtures thereof, depending on the conditions of the aromatization process.

TABLE 2

Material balances of aromatization.

| | Example No. | | | | | | |
|---|---|---|---|---|---|---|---|
| | 3 | 4 | 5 | 6 | 7 | 9 | 10 (comp) |
| Catalyst according to example No. | 1 | 2 | 1 | 1 | 1 | 2 | 2 |
| Temperature, ° C. | 500 | 490 | 400 | 500 | 480 | 450 | 520 |
| Pressure, atm | 18 | 8 | 4 | 6 | 1 | 6 | 8 |
| Space velocity of gas supply, h$^{-1}$ | 300 | 1000 | 500 | 300 | 300 | 1500 | 300 |
| Feedstock composition, vol. % | | | | | | | |
| n-butane | 100 | | | | | | |
| WFLH | | 100 | | | 75 | | |
| methanol | | | 100 | 30 | 25 | | |
| Propane-butane fraction (PBF) | | | | 70 | | | 100 |
| Propane-propylene fraction (PPF) + butane-butylene fraction (BBF) (50/50 vol.) | | | | | | 80 | |
| isopropanol | | | | | | 20 | |
| TOTAL: | 100 | 100 | 100 | 100 | 100 | 100 | 100 |
| Conversion of oxygenates, % | — | — | 100 | 100 | 100 | 99.8 | — |
| AHCC yield per pass of feedstock (for the H/C portion of the feedstock*), wt. %. | 34.6 | 46.4 | 50.5* | 38.1* | 52.2* | 78.2* | 29.2 |
| Gas composition, wt. % | | | | | | | |
| CH$_4$ | 17.3 | 6.8 | 17.1 | 14.3 | 10.0 | 6.8 | 43.7 |
| C$_2$H$_6$ | 18.2 | 25.9 | 5.0 | 10.6 | 17.3 | 20.8 | 24.6 |
| C$_2$H$_4$ | 0.1 | 0.3 | 11.5 | 5.8 | 5.9 | 3.3 | trace |
| C$_3$H$_8$ | 35.7 | 37.1 | 26.4 | 32.2 | 31.8 | 32.1 | 25.0 |
| C$_3$H$_6$ | 0.2 | 0.5 | 12.0 | 8.1 | 6.3 | 4.5 | 0.2 |
| i-C$_4$H$_{10}$ | 2.0 | 10.5 | 8.9 | 5.5 | 9.7 | 10.5 | 1.1 |
| n-C$_4$H$_{10}$ | 23.7 | 15.0 | 12.6 | 18.2 | 13.8 | 18.3 | 1.9 |
| C$_4$H$_8$ | 0.2 | 0.8 | 4.2 | 2.2 | 2.5 | 2.7 | 0.1 |
| H$_2$ | 2.6 | 3.1 | 1.7 | 2.9 | 2.6 | 1.0 | 3.4 |
| CO$_x$ | — | — | 0.6 | 0.2 | 0.1 | — | — |
| Total, wt. % | 100 | 100 | 100 | 100 | 100 | 100 | 100 |
| Composition of AHCC, wt. %, including: | | | | | | | |
| aliphatic substances | 0.9 | 19.2 | 0.8 | 0.4 | 1.2 | 8.2 | 0.9 |
| benzene | 14.9 | 12.0 | 7.5 | 8.2 | 7.8 | 6.1 | 21.0 |
| toluene | 30.1 | 30.8 | 36.4 | 27.8 | 24.8 | 32.2 | 37.1 |
| xylenes + ethylbenzene | 31.9 | 22.8 | 44.6 | 41.6 | 38.1 | 36.4 | 22.7 |
| alkyl aromatics C$_{9+}$ | 22.2 | 15.2 | 10.7 | 22.0 | 28.1 | 18.1 | 18.3 |
| Total ArH in the AHCC composition: | 99.1 | 80.8 | 99.2 | 99.6 | 98.8 | 91.8 | 99.1 |
| Time for 20% reduction in the ArH yield, h | | | | | 270 | | 185 |

*since oxygenates (oxygen-containing alcohols) are used in the feedstock composition, the AHCC yield is calculated for the H/C portion of the feedstock (as, for example, in the methanol molecule - CH$_3$OH, the hydrocarbon portion is CH$_2$, i.e. it makes up 43.8 wt. %).

The technical result obtained by carrying out the proposed invention involves achieving an increased yield of AHCC (in one pass of feedstock without recirculating the separation gases) and increased selectivity for xylenes. Thus, comparing the indicators of the propane-butane fraction aromatization reaction according to the proposed method (example number 6) with the addition of an oxygenate (methanol) to the H/C feedstock with the prior art (comparative example number 10, without oxygenate additives), it is evident that with the catalyst proposed in the claimed invention, at a lower temperature (500 instead of 520° C.) and pressure (6 instead of 8 atm) a higher yield of AHCC is obtained in one pass of the feedstock (38.1% versus 29.2%). Furthermore, the ArH composition according to the proposed method is dominated by widely sought-after xylenes (the concentration of the $C_8$ aromatic fraction in the composition of the AHCC is up to 41.6%), while, in example 10, the concentration thereof does not exceed 22.7%.

A similar picture is also observed during aromatization of WFLH. From the comparison of examples no. 7 and 4, it is obvious that the addition of 25 vol. % methanol to the H/C feedstock leads to an increase in the AHCC yield of 5.8%, wherein the concentration of the $C_8$ fraction, containing xylenes, in the AHCC composition increases from 22.8 to 38.1%; furthermore, atmospheric pressure is used, and the temperature of the process in example number 7 (with the addition of the oxygenate) is 10° C. lower. It should be noted that during joint treatment of an olefin-containing mixed fraction (PPF+BBF) and isopropanol (example number 9), the AHCC yield reaches 78.2% even at the relatively low temperature of 450° C.

A significant result of the proposed invention is that mixing the gaseous H/C feedstock with oxygenates eliminates the need to pre-heat same to a temperature of approximately 550-575° C., as is done in the prior art invention during the aromatization of the propane-butane fraction, because during the conversion of the oxygenates, additional heat is given off which is required for carrying out the aromatization reaction. The streams of feedstock at the inlet to the reactor should be heated only to 150-250° C., and this can be provided for by recovering the heat from the hot gas stream of the product at the outlet from the reactor, which makes it possible to avoid using multiple-section furnaces (combustion heaters).

The proposed method eliminates the need to convert individual $C_{3+}$ and $C_{5+}$ H/C in separate successive zones with a different temperature mode, as well as the need to recirculate gases. This leads to a significant reduction in energy consumption while simultaneously simplifying the technological implementation of the process.

Furthermore, in the proposed method for the aromatization of $C_3$-$C_4$ gases, low-octane H/C fractions and aliphatic alcohols as well as mixtures thereof, the period of stable operation of the catalyst is significantly extended because reaction water is formed during the conversion of the oxygenates, and the process takes place under milder conditions (in terms of temperature and pressure). This is affirmed by the time for a 20% reduction in the yield of ArH, which is presented in table 2, and which according to the proposed method increases by at least 1.5 times.

The invention claimed is:

1. A method for the aromatization of a gaseous feed, the method comprising:
   a) contacting the gaseous feed with a catalyst mixture in a bed of a reactor to produce an aromatization product, wherein the gaseous feed comprises a mixture of hydrocarbons and aliphatic alcohols, where the hydrocarbons are selected from a mixture of $C_3$-$C_4$ paraffins and olefins, a mixture of $C_1$-$C_8$ paraffins, and a naphtha fraction with a final boiling point of 200° C., and the aliphatic alcohols are selected from the group consisting of $C_1$-$C_3$ aliphatic alcohols, and wherein the catalyst mixture is selected from the group consisting of:
   i) a catalyst comprising a first pentasil, a second pentasil and a binder comprising silicon oxide, wherein:
      the first pentasil zeolite comprises a $SiO_2/Al_2O_3$ ratio=20 and 0.5 to 2.0 wt % of a rare earth element based on the mass of the first pentasil zeolite,
      the second pentasil zeolite comprises a $SiO_2/Al_2O_3$ ratio=82, 0.04 wt % sodium oxide, and 0.5-5.0 wt % magnesium oxide,
      a mass ratio of first pentasil zeolite to second pentasil zeolite is between 1.7 and 2.8, and
      the binder is between 20 to 25 wt % of the mass of the catalyst;
   ii) a catalyst comprising a first pentasil, a second pentasil and a binder comprising silicon oxide and aluminum oxide, wherein:
      the first pentasil zeolite comprises a $SiO_2/Al_2O_3$ ratio=20 and 0.5 to 2.0 wt % of a rare earth element based on the mass of the first pentasil zeolite,
      the second pentasil zeolite comprises a $SiO_2/Al_2O_3$ ratio=82, 0.04 wt % sodium oxide, and 0.5-5.0 wt % magnesium oxide,
      a mass ratio of first pentasil zeolite to second pentasil zeolite is between 1.7 and 2.8, and
      the binder is between 20 to 25 wt % of the mass of the catalyst;
   iii) a catalyst comprising a first pentasil, a second pentasil and a binder comprising silicon oxide and aluminum oxide, wherein:
      the first pentasil zeolite comprises a $SiO_2/Al_2O_3$ ratio=20 and 0.5 to 2.0 wt % of a rare earth element based on the mass of the first pentasil zeolite,
      the second pentasil zeolite comprises a $SiO_2/Al_2O_3$ ratio=82, 0.04 wt % sodium oxide, and 0.5-5.0 wt % magnesium oxide,
      a mass ratio of first pentasil zeolite to second pentasil zeolite is between 1.7 and 2.8,
      the binder is between 20 to 25 wt % of the mass of the catalyst
      and the aluminum oxide does not exceed 25 wt % of the mass of the binder; and
   b) maintaining the catalyst mixture bed at a reaction temperature of 400-500° C. during the contacting;
      wherein coking is reduced and xylenes production is increased.

2. The method of claim 1, wherein the reactor is maintained at a pressure of 1-18 atm.

3. The method of claim 1, wherein no recirculation of gases occurs.

4. The method of claim 1, wherein the gaseous feed is pre-heated to a temperature of 15-250° C.

5. The method of claim 1, wherein the gaseous feed is supplied at a gas volumetric space velocity of 300-1500 $h^{-1}$.

6. The method of claim 1, wherein the aliphatic alcohols are diluted with water.

7. The method of claim 1, wherein the mixture of hydrocarbons and aliphatic alcohols has an oxygenate content of between 10 to 50 vol. %.

* * * * *